(12) United States Patent
Terwee et al.

(10) Patent No.: US 8,734,463 B2
(45) Date of Patent: May 27, 2014

(54) METHOD OF IMPLANTING AN INTRAOCULAR LENS

(75) Inventors: Thomas Henricus Marie Terwee, Roden (NL); Hendrick Albert Weeber, Groningen (NL); Patricia Ann Piers, Groningen (NL)

(73) Assignee: AMO Groningen B.V., Groningen (NL)

( * ) Notice: Subject to any disclaimer, the term of this patent is extended or adjusted under 35 U.S.C. 154(b) by 1236 days.

(21) Appl. No.: 11/564,783

(22) Filed: Nov. 29, 2006

(65) Prior Publication Data

US 2007/0106380 A1 May 10, 2007

Related U.S. Application Data

(60) Continuation of application No. 10/436,307, filed on May 12, 2003, now Pat. No. 7,156,101, which is a division of application No. 09/865,009, filed on May 24, 2001, now Pat. No. 6,598,606.

(60) Provisional application No. 60/209,082, filed on Jun. 2, 2000.

(51) Int. Cl.
 *A61F 9/00* (2006.01)
 *A61F 11/00* (2006.01)

(52) U.S. Cl.
 USPC .......................................... 606/107; 606/108

(58) Field of Classification Search
 USPC .................. 128/898; 600/318–321, 356–360, 600/398–406; 606/107; 623/6.11–6.13, 623/6.56–6.59, 902, 907
 See application file for complete search history.

(56) References Cited

U.S. PATENT DOCUMENTS

| | | | |
|---|---|---|---|
| 4,542,542 A | 9/1985 | Wright | |
| 4,573,998 A | 3/1986 | Mazzocco | |
| 4,608,050 A | 8/1986 | Wright et al. | |
| 4,685,921 A | 8/1987 | Peyman | |
| 4,836,202 A * | 6/1989 | Krasner | 606/107 |
| 4,919,151 A | 4/1990 | Grubbs et al. | |
| 4,950,289 A | 8/1990 | Krasner | |
| 5,224,957 A | 7/1993 | Gasser et al. | |
| 5,278,258 A | 1/1994 | Gerace et al. | |
| 5,391,590 A | 2/1995 | Gerace et al. | |
| 5,476,514 A | 12/1995 | Cumming | |
| 5,728,155 A * | 3/1998 | Anello et al. | 623/6.47 |
| 6,051,024 A * | 4/2000 | Cumming | 623/6.44 |
| 6,164,282 A | 12/2000 | Gwon et al. | |
| 6,176,878 B1 | 1/2001 | Gwon et al. | |
| 6,197,059 B1 | 3/2001 | Cumming | |
| 6,361,561 B1 * | 3/2002 | Huo et al. | 623/6.56 |
| 6,387,126 B1 | 5/2002 | Cumming | |
| 6,638,306 B2 | 10/2003 | Cumming | |
| 2004/0243233 A1 | 12/2004 | Phillips | |

FOREIGN PATENT DOCUMENTS

| | | |
|---|---|---|
| EP | 0414219 | 2/1991 |
| WO | WO 9947185 | 9/1999 |
| WO | WO 0022459 | 4/2000 |
| WO | WO 0022460 | 4/2000 |
| WO | WO 0044379 | 8/2000 |

OTHER PUBLICATIONS

Nishi et al. "Controlling the Capsular Shape in Lens Refilling", Arch Ophthalmol. 115:507-510 (1997).
Hettlich et al."Light-induced endocapsular polymerization of injectable lens refilling materials" German J. Ophthalmol., 1:346-349 (1992).
O'Donnell, Jr., et al. "Intraoperative Autorefraction: Avoiding Intraocular Lens Power Surprises", J. Cataract Refract. Surg., 15:597-598 (1989).

* cited by examiner

*Primary Examiner* — David Isabella
*Assistant Examiner* — Joshua Levine
(74) *Attorney, Agent, or Firm* — AMO Groningen B.V.

(57) ABSTRACT

A method for implanting an intraocular lens into the eye of a subject includes placing the intraocular lens into the eye of a subject and administering a drug in an amount sufficient to maintain an accommodative state of the eye. The method further includes permitting at least a portion of the intraocular lens to become coupled to at least a portion of the eye while maintaining the eye in the accommodative state. In certain embodiments, the method may include forming an intraocular lens while maintaining an accommodative state of the eye. In such embodiments, the method may exclude permitting at least a portion of the intraocular lens to become coupled to at least a portion of the capsular bag.

6 Claims, No Drawings

METHOD OF IMPLANTING AN INTRAOCULAR LENS

RELATED APPLICATIONS

This application is a continuation of U.S. application Ser. No. 10/436,307, filed May 12, 2003, which was a divisional of U.S. application Ser. No. 09/865,009, filed May 24, 2001, now U.S. Pat. No. 6,598,606, issued Jul. 29, 2003, which claimed priority under 35 U.S.C §119(e) to provisional application No. 60/209,082, filed on Jun. 2, 2000.

BACKGROUND OF THE INVENTION

1. Field of the Invention

The present invention relates generally to methods of implanting an accommodating intraocular lens, and more specifically to implanting an accommodative intraocular lens wherein the accommodative state of the eye is controlled for a period of time before, during, and/or after a surgery.

2. Description of the Related Art

In the field of ophthalmic cataract surgery, wherein a defective natural lens is replaced with an artificial lens, there has been a development towards lenses and methods that inflict less surgical trauma and that provide accommodation (e.g., provide a focal point that is regulated by action of the ciliary muscle in the eye). For many years most of the IOLs were made of polymethylmethacrylate (PMMA), a material with good optical characteristics and compatibility with tissues in the eye. A disadvantage of PMMA, however, is that it is a very rigid material and a surgical incision must be made large enough, generally at least 5-6 mm, for the implantation of the lens. With improved devices for removal of the natural lens by phacoemulsification, requiring only a rather small incision, there was a need for lenses with foldable optics, as disclosed in the U.S. Pat. No. 4,573,998 (Mazzocco).

Even with the mentioned types of improved implantable IOLs, now available on the market, there is still a desire to obtain a lens which admits the use of an even smaller incision and behaves like the natural lens in the eye, i.e. will be accommodating with a focal point regulated by action of the ciliary muscle in the eye. In order to allow for a really small incision it would be necessary to form the lens inside the eye from a solution which is injected into the capsular bag or into a balloon placed inside the bag by means of a standard injection needle.

Another area of development in the field is the incorporation of accommodative IOLs, i.e., IOLs that at least partially restore the ability of the eye to focus both at near and distant objects. One approach for implanting an accommodating IOL is to form the IOL of a material that can be injected into and formed in the eye to provide a soft lens that is deformable in response to the ciliary muscle. Examples of IOLs formed from an injected solution of a silicone prepolymer, crosslinker and catalyst have already been suggested in U.S. Pat. Nos. 5,278,258 and 5,391,590 (Gerace et al), both of which are herein incorporated by reference. Other examples of injectable materials are disclosed in U.S. Pat. Nos. 4,542, 542; 4,608,050 (Wright et al); and International patent application PCT/EP99/04715, all herein incorporated by reference.

In another approach, the accommodative IOL is formed prior to placement into the eye as disclosed, for example, in U.S. Pat. No. 6,443,985 (Woods), U.S. Pat. No. 6,846,326 (Zadno-Azizi et al.), U.S. Pat. No. 6,616,692 (Glick et al.), U.S. Pat. No. 6,488,708 (Sarfarazi), all herein incorporated by reference. Accommodative IOLs formed prior to placement in the eye are generally larger than monofocal or multifocal IOLs with equivalent optical power, thereby creating a greater need for foldable optical materials.

Accommodating IOLs, whether formed from a solution that is injected into the capsular bag or pre-formed for subsequent placement into the capsular bag, may be fabricated to have either an accommodative bias or a disaccommodative bias. When an accommodating IOL is fabricated with a disaccommodative bias, the IOL is configured to provide distant vision when the lens is in its natural or unstressed state. When the accommodating IOL is fabricated with an accommodative bias, the IOL is disposed to provide near or accommodated vision when the lens is in its natural or unstressed state. In both cases, it may be advantageous to maintain the eye in a predetermined state of accommodation during a post-operative time period over which cell growth onto at least portions of the IOL is used to secure the IOL to capsular bag or other parts of the eye.

U.S. Pat. No. 6,197,059 discloses an accommodating IOL having a generally disaccommodative bias. After implantation of the IL, the ciliary muscle is maintained in its relaxed state by the use of a cycloplegic to prevent dislocation of the IOL The cycloplegic may be initially introduced into the eye at the start of surgery to dilate the pupil and paralyze the ciliary muscle in its relaxed state. After surgery, cycloplegic drops are preferably introduced into the eye by the patient during a postoperative healing period while the anterior capsular remnant fuses to the posterior capsule of the bag. Once the cycloplegic effect wears off the ciliary muscle may again contract to move the optic anteriorly and provide near or accommodated vision.

However, this approach is ineffective for use with accommodating IOLs that are either injected into the eye or are otherwise implanted in an accommodative state. In such cases, the use of cycloplegic substances, as taught in the '059 patent are ineffective or even counterproductive, since such substances maintain the eye in a relaxed or disaccommodative state while the lens is in the accommodative state. Other approaches and methods are, therefore, needed that allow formation or placement of intraocular lenses having an accommodative bias in the eye.

SUMMARY

The present invention generally provides methods of implanting an accommodating intraocular lens wherein the accommodative state of an eye is controlled for a period of time before, during, and/or after a surgery. One aspect of the present invention involves a method of implanting an accommodating intraocular lens comprising placing an intraocular lens into a capsular bag of an eye of a subject. The method also comprises administering a drug in an amount sufficient to maintain an accommodative state of the eye. The method further comprises permitting at least a portion of the intraocular lens to become coupled to at least a portion of the capsular bag while the eye is in the accommodative state. In certain embodiments, the method may include forming an intraocular lens while maintaining an accommodative state of the eye. In such embodiments, the method may exclude permitting at least a portion of the intraocular lens to become coupled to at least a portion of the capsular bag.

The intraocular lens is preferably an accommodating intraocular lens having an accommodative bias. In one aspect of the invention, the intraocular lens is adapted to move axially in the eye between the accommodative state and a disaccommodative state through the use of one or more haptics or a positioning structure of some type that move a lens axially within the eye. In certain embodiments, the intraocular lens may additionally or alternatively be adapted to produce a disaccommodative state by changing a surface shape thereof when the intraocular lens is disposed within the eye, for example by injecting a solution of a silicone prepolymer, crosslinker and catalyst, or by forming the lens of a resilient material that can change shape due to ocular forces such as movement of the ciliary muscles and/or capsular bag.

In another aspect of the present invention, the drug is administered topically to the eye in a pharmaceutically acceptable ophthalmic formulation. Where the eye includes a ciliary muscle, the administering is preferably effective to contract the ciliary muscle. In yet another aspect of the present invention, coupling includes fibrosis. Alternatively or additionally, the intraocular lens may comprise a polymer material adapted to adhere to the capsular bag, for example an amphiphilic block copolymer, wherein coupling may additionally or alternatively include adhering at least a portion of the intraocular lens to the capsular bag.

In still another aspect of the present invention, the drug is a muscarinic agent such as a muscarinic agonist. The muscarinic agonist may be selected from the group consisting of pilocarpine, isopilocarpine lactam, carbachol, bethanechol, methacholine and muscarine. In yet another aspect of the present invention, the muscarinic agent is a muscarinic antagonist. For example, in certain embodiments, the muscarinic agent is a muscarinic antagonist that is selected to act on M1 receptor subtype of a ciliary muscle of the eye, for example a muscarinic antagonist selected from the group consisting of pirenzepine, telenzepine and trihexyphenidyl. In certain embodiments, the muscarinic agent is a muscarinic antagonist that is selected to act on M2 receptor subtype of a ciliary muscle of the eye, for example a muscarinic antagonist selected from the group consisting of (+) (11-({2-[diethylaminomethyl]-1-piperdidinyl}acetyl)-5,11-di-hydro-6H-pyrido(2,3-b) (1,4)benzodiazepine-6-one and (+)4,11 dihdro-11-{[(2-[dipropylamino)methyl]-1-piperidinyl)amino] carbonyl}-6H-pyrido(2,3-b) (1,4)benzodiazepine-6-one. In yet other embodiments, the muscarinic agent is a muscarinic antagonist that is selected to act on M3 receptor subtype of a ciliary muscle of the eye, for example a muscarinic antagonist selected from he group consisting of diphenylacetoxy-N-methylpiperidine methiodide and (+) p-fluro-hexahydro-siladifenidol hydrochloride. In still other embodiments, the muscarinic agent is a muscarinic antagonist is selected to act on M4 receptor subtype of a ciliary muscle of the eye, for example selected from the group consisting of pirenzepine and telenzepine.

In yet another aspect of the present invention, a method of implanting an accommodating intraocular lens comprises placing an intraocular lens into a capsular bag of an eye of a subject and maintaining the eye in an accommodative state. The method also comprises permitting at least a portion of the intraocular lens to become coupled to at least a portion of the capsular bag while maintaining the eye in the accommodative state.

DETAILED DESCRIPTION

In certain embodiments, a method of implanting an intraocular lens comprises forming, injecting, or placing an intraocular lens into an eye of a subject, for example into a capsular bag of the eye, and maintaining the eye in an accommodative state. Alternatively, the intraocular lens may be implanted in another portion of the eye such as in direct contact with the ciliary muscle of the eye. The method additionally comprises administering a drug in an amount sufficient to maintain an accommodative state of the eye. The method further comprises permitting at least a portion of the intraocular lens to become coupled or attached to at least a portion of the capsular bag or some other part of the eye while the eye is in the accommodative state.

As used herein, the term "accommodative state" means a state of the eye and/or ciliary muscle of a subject in which the ciliary muscle is contracted by an amount sufficient to provide intermediate vision or near vision, or contracted by an amount that is substantially equivalent to the amount of ciliary muscle contraction a subject is capable of producing given their age and the physiological state of their eye. By contrast, as used herein, the term "disaccommodative state" means a state of the eye and/or ciliary muscle in which the ciliary muscle is relaxed to an extent to provide distant vision to the extent allowable given the physiological state of their eye. As used herein the term "near vision" means vision of objects situated approximately 25-40 centimeters from either the eye or spectacle plane. As used herein the term "intermediate vision" means vision of objects situated approximately 40 centimeters to approximately 1.5 meters from the eye or spectacle plane. As used herein, the term the term "near vision" means to vision produced by an eye that allows a subject to focus on objects or planes that are relatively close to the subject, preferably within a range of about 30 cm or at a distance at which a subject would generally place printed material for the purpose of reading. As used herein, the term "distant vision" means vision produced by an eye that allows a subject to focus on objects or planes that are relatively distant from the subject, preferably at a distance that is greater than about 1 meter to about 2 meters away from the subject, more preferably at a distance of 5 to 6 meters or greater.

In certain embodiment, the method of implanting an intraocular lens comprises placing an intraocular lens in the capsular bag or some other portion of the eye, wherein the intraocular lens is at least partially formed prior to implantation into the eye. Preferably, the intraocular lens is formed to have an accommodative bias. As used herein with regard to an accommodating intraocular lens, the term "accommodative bias" refers to the state of an intraocular lens wherein the lens is configured to provide near or intermediate vision when the lens is in its natural or unstressed state. By contrast, the term "disaccommodative bias" refers to the state of an intraocular lens wherein the lens that is configured to provide distant vision when the lens is in its natural or unstressed state.

The intraocular lens may take any of the forms discussed above herein under Background of the Invention, or may incorporate other structures or features for providing accommodation. For example, in one useful embodiment, the intraocular lens comprises an optic that changes shape in response to the ciliary body movement to provide accommodation, as disclosed in U.S. patent application Ser. Nos. 10/280,918 and/or 10/736,431 (Woods et al.), herein incorporated by reference. In other embodiments, the intraocular lens is configured to inhibit cell growth on the optic portion of the intraocular lens, for example, as disclosed in U.S. patent application Ser. No. 10/736,431 (Woods et al.), herein incorporated by reference.

When the intraocular lens is placed in the eye, placement may be accomplished using tweezers, an inserter device, or any devices or means available to the surgeon for inserting an intraocular lens into the eye of a subject. The intraocular lens may be placed within the eye either as a single unit or as at least two separate parts that are subsequently assembled inside the eye by a surgeon.

Before, during, and/or after placement of the intraocular lens into the eye, the above implantation method also comprises administering a drug in an amount sufficient to maintain an accommodative state of the eye. In certain embodiments, administering the drug comprises topical administration of the drug onto the eye in the form of a pharmaceutically acceptable ophthalmic formulation that stimulates the ciliary muscle. In other embodiments, administering the drug comprises coating at least portions of the intraocular lens with a bio-absorbable coating containing a pharmaceutically acceptable ophthalmic formulation and then allowing the formulation to be absorbed by the eye after the intraocular lens is implanted into the eye. In yet other embodiments, administering the drug comprises inserting the drug into the eye, for example, in the form of capsule, such that the drug is absorbed by the eye over period of time. For instance, a bio-absorbable capsule may be placed into the eye before, during, and/or during a surgery and disposed on or near the intraocular lens to dissolve over a period of time and continually provide an effective drug level for maintaining the eye in an accommodative state. In yet other embodiments, administering the drug comprises inserting the drug in a drug delivery vehicle, for example a biodegradable or non-biodegradable device that may be placed into or on the eye.

The method of implanting an intraocular lens also includes permitting at least a portion of the intraocular lens to become coupled or attached to at least a portion of the capsular bag while the eye is in the accommodative state. For example, coupling between the intraocular lens and the capsular bag may be accomplished by allowing the eye to heal after a surgery while the eye is maintained in an accommodative state over a period of time of at least a few hours, preferably a period of time of several days to at least about two week. In certain embodiments, the period of time is greater than two weeks and may be at least about two months to as long as about six months.

In certain embodiment, at least a portion of the intraocular lens may fuse or attach to a portion of the eye by fibrosis during postoperative healing period. As used herein, the term "fibrosis" refers to the formation of fibrous tissue within the capsular bag. For example, the at least a portion of the intraocular lens may attach to a portion of the capsular bag, such as the anterior capsular remnant, or to a portion of the zonules or ciliary muscle. The intraocular lens preferably comprises at least one haptic that is used to center and/or stabilize the intraocular lens within the eye and may additionally be used to provide at least some accommodative motion of the intraocular lens. In other embodiments, the intraocular lens comprises a polymer material that is adapted to adhere to a portion of the eye, preferably the capsular bag. For example U.S. Provisional Application No. 60/638,051, herein incorporated by reference, discloses an amphiphilic block copolymer or tissue intermediate polymer (TIP) that is compatible such embodiments of the present invention. In such embodiments, at least a portion of the intraocular lens coupled to the capsular bag by adhesion while the capsular bag is maintained in the accommodative state.

In other embodiments, the method of implanting the intraocular lens comprises forming an intraocular lens from a polymerizable fluid. For example, in one embodiment, a method of implanting an accommodating intraocular lens comprises pre-selecting a polymerizable fluid to be introduced into the capsular bag and formed into a replacement lens. Typically, the natural lens to be replaced suffers from cataract formation, but also presbyopic lenses, i.e., lenses having completely or partially lost their capacity of accommodation, may be replaced. When a polymerizable fluid is used, the intraocular lens is preferably capable of being formed by means of one or several polymerization reactions.

The resulting lens is intended to provide the eye with a determined desired refractive outcome value estimated as optically suitable or ideal for the individual elected to undergo surgery. The pre-selection method comprises measuring of selected eye dimensions including corneal curvature (anterior or posterior curves or both), the axial length of the eye and the anterior chamber depth. The person skilled in this technology is knowledgeable of several measurement methods to obtain this information and thereby finding relevant information about the eye, including the refractive value of the cornea. From these values the shape and the volume of capsular bag is estimated and thereby it is possible to calculate the quantity and refractive index of the polymerizable fluid to be introduced in the capsular bag in order to obtain a refractive value that sufficiently complies with the desired refractive outcome value of the individual eye. Typically, such calculations comprise the determination of a lens model refractive value (the refractive value necessary for the lens to restore the vision) from the measured corneal refractive value and the desired refractive outcome value. By further estimating the shape and thereby the volume of the individual capsular bag together with lens model refractive value, a quantity of polymerizable fluid with a specific refractive index is determined. According to one embodiment of the method, a polymerizable fluid then is selected from a kit of polymerizable fluids with a range of different refractive indices. In practical terms, the surgeon can select the determined quantity of the fluid of the kit having a refractive index value, which is most compatible to the estimated value of the refractive outcome value. Alternatively, a polymerizable fluid having an identical refractive index value to what has been estimated can be ordered from a manufacturer. Preferably, such kits of polymerizable fluids will have a range of refractive indices varying from about 1.39 to about 1.6. As discussed in more detail below, several suitable polymerizable fluids are conceivable for the kit which comply with such requirements as being easy to inject with conventional equipment, having suitably high specific gravity and providing options to obtain suitably high refractive indices and yet obtaining desirable mechanical characteristic for intraocular lenses after polymerization, including sufficiently low modulus to obtain an implanted lens, that can undergo accommodation when influenced by the ciliary muscles of the eye. The kit can typically comprise a range of such fluids filled in multi-compartment containers, separately stored from agents necessary to bring about the polymerization. Advantageously, the multi-compartment containers are provided with means to establish fluid communication between the containers just prior to the administration into the capsular bag and with means, either to inject the fluid, or to operate on the container with a conventional injection device. Many such containers are known to the skilled person and will not be described herein in more detail.

In other embodiments, a method of restoring the vision of an eye comprises removing an impaired lens from the capsular bag and replacing said lens with a quantity of a polymerizable liquid with the purpose of forming an intraocular lens with a predetermined refractive outcome. The defective natural lens is preferably removed by state of the art surgical interventions including an eye opening with a small incision (about 1 mm), capsulotomy with capsulorhexis (about 1 mm) and lensectomy (removal of the natural lens) for example with phacoemulsification. Optional measures taken after finalizing the lensectomy can include conventional methods to preserve the capsular integrity and preparing the capsule, such as cleaning and anti-PCO treatment.

Embodiments of the present invention include the determination of a desired refractive outcome value suitable for the eye, which is performed according to standard optical procedures, which may have been performed at an earlier occasion than the remaining steps of the method. Frequently, the desired refractive outcome of the patient is an emmetropic eye. The method further comprises the steps of introducing the polymerizable solution into the capsular bag and thereafter determining the refractive value of the eye. This refractive value is then if necessary compared with the desired refractive outcome value. The refractive value of the eye with the polymerizable fluid introduced in the capsular bag is then adjusted to obtain a value that complies with said desired value of refraction. In this context complying values means that they at best completely coincide with an accuracy relevant to the applied measuring means, or that the values sufficiently conform to each other considering what is clinically applicable in the present case. Further in this context, adjusting the refractive value of the eye will mean that the lens system of the capsular bag and polymerizable solution is affected, so as to bring about a sufficient change in eye refraction, such that said requested compliance is obtained. It is to be understood that the comparison of the mentioned refractive values and the subsequent adjustment if necessary can be repeated one or several times in an iterative process, so as to approach sufficiently complying refractive values. In such a repetitive process, it is also to be understood that different measures to adjust the refraction can be considered in each adjusting procedure. As will be explained below, the present invention introduces several alternatives to provide such adjustments by affecting the mentioned provisional lens system and thereby obtaining refractive control of the eye during the formation of the intraocular lens. When sufficiently complying values are obtained, the formation of a lens implant from the polymerizable liquid is initiated by starting a polymerization reaction from the constituents of the fluid. As a part of the formation process, it also intended that the polymerization can be performed in one or several steps with intermediate control of the refraction of the eye and if necessary refraction adjustments can be made in accordance with what has been described above. The refractive values of the eye as performed in the method after introducing the polymerizable fluid in the capsular bag can be made with on-line refractometry, for example as outlined in Journ. Cataract. Refract. Surg., 1989, Vol. 15, pp. 597-8.

According to a preferred embodiment, the polymerizable solution is pre-selected in accordance with what has been described in the foregoing part. Alternatively, a polymerizable fluid can be directly selected on the basis of other criteria.

In some embodiments, it is also preferable to direct a rinsing fluid into the anterior chamber of the eye. The rinsing fluid is conventionally employed during cataract surgery in the process of lensectomy by introducing a probe in the anterior chamber of the eye. As will be discussed later, the rinsing fluid can be employed in the refractive control of the eye during lens formation. In the present method, the rinsing fluid is a saline solution provided with a specific refractive index. It is preferable that the polymerizable fluid is introduced in the capsular bag by means of injection, suitably through the orifice already created in the wall during the removal of the impaired natural lens. For this purpose, it is a prerequisite that the polymerizable fluid has a sufficiently low viscosity so it can be efficiently injected through a standard cannula with an 18 Gauge needle or finer. Preferably, the polymerizable fluid has a viscosity below about 60000 cSt and more preferably, below about 8000 cSt.

According to one aspect of the invention, the polymerizable fluid comprises a polymerizable polysiloxane composition, suitably also comprising a crosslinking agent to participate in the polymerizing forming process, i.e. a crosslinking process. According to one alternative of this aspect, the polysiloxane composition further comprises a catalyst activated by heat to initiate the crosslinking process. In another alternative, the polysiloxane composition comprises a photoinitiator that suitably is activated by visible light, in particular blue light. A useful polysiloxane composition can be found in the International Patent Application PCT/E-P99/07780 that describes silicone compositions adapted for being thermocured in the capsular bag with a suitable high density above 1.0 g/cm$^3$. The polymerization after injection such a composition can be initiated by raising the temperature of the rinsing fluid to a value necessary to activate the catalyst driven polymerization. Typically, such an increase in temperature can be from about 20 to about 40° C. Alternatively, it is conceivable to use the photocurable compositions designed for intraocular lens production directly in the capsular bag of the eye, as described in the International Patent Application PCT/EP99/04715. From the teachings of these documents, the skilled person can readily obtain a wide range of polymerizable polysiloxane compositions suitable for injection into the capsular bag, having a range of different refractive indices varying from about 1.39 up to 1.6, as is suitable for the above-mentioned kit for selecting an appropriate polymerizable fluid. Both these documents, which herewith are incorporated as references in their entirety, provide polysiloxanes designed for injection into the capsular bag which by a specific selection of substituents on the polysiloxane backbone enables suitable variation range in refractive index, while still retaining characteristics of sufficiently high density (preferably higher than about 1.0 g/cm$^3$) and excellent mechanical characteristics for lens production.

According to an alternative aspect, the polymerizable fluid comprises an aqueous composition of a hydrophilic polymer carrying sites for crosslinking, wherein said aqueous composition further comprises a crosslinker. Preferably, the formation of a lens implant is initiated by activating a photoinitiator by irradiation of a predetermined wavelength or range of wavelengths. Most suitable in the context of the present method is to select a photoinitiator activated by visible light, preferably blue light. Examples of such compositions are found in the International Patent Application published as WO 99/47185, wherein crosslinkable hydrophilic units of different polymers are disclosed.

As earlier mentioned the inventive method may include controlling the refraction of the eye by performing refraction adjustments of the system consisting of the capsular bag containing the polymerizable fluid.

According to one embodiment, the refractive value of the eye is adjusted by changing the pressure exerted on the capsular bag. A pressure change will result in that shape of the capsular bag is altered and thereby the curvature of its refractive surfaces. Varying the pressure exerted on the capsular bag is preferably performed by altering the pressure of the rinsing fluid as introduced in the anterior chamber of the eye with probe in fluid connection with a supply container. Accordingly, the fluid pressure of the rinsing liquid can conveniently be controlled by heightening or lowering the supply container as correlated to scale of height and pressure (mm Hg). The flowing rinsing fluid can thereby directly be used to exert different and readily controllable pressures on the anterior side of the capsular bag and thereby model its overall shape and its refractive value.

According to another embodiment, the refractive value of the eye is adjusted by affecting the state of accommodation and thereby obtaining control of the shape of the capsular bag. In a more accommodated state, the capsular bag with the fluid lens material is more rounded, whereas a less accommodated state of the lens results in a more flattened shape of the capsular bag. The different states of accommodation are caused by stretching and relaxation of the capsular bag by zonulas as influenced by the contraction and relaxation of the ciliary muscles. Several alternatives are conceivable to affect the state of accommodation. One alternative, discussed in greater detail below herein, is either local or systemic administration of drugs, which influence the state of the ciliary muscles, such as pilocarpine. Another alternative to affect the state of accommodation is to visually stimulate the fellow eye not elected to surgery. The inadvertent accommodation following in the eye subjected to surgical intervention can thereby used for refractive adjustment.

According to a further embodiment, the refractive value of the eye is adjusted by changing the pressure inside the capsular bag. Suitably, such an adjustment is accomplished by changing the volume of the polymerizable solution. The volume can be adjusted either by re-introducing or withdrawing fluid from the capsular bag. Preferably, this is performed by means of an injection device through the previous injection site. It is also conceivable to accomplish changes in the fluid volume by letting the fluid swell or shrink in a controlled manner. It is to be understood that the different embodiments of adjusting the refraction can be combined in various manners. When conducting the inventive method, the surgeon will have the possibility to employ one way of affecting the capsular shape, thereafter controlling the refractive value, and if necessary for complying with the predetermined value use another embodiment of adjusting the refraction.

When starting the formation of the lens implant, a polymerizing process is initiated in the capsular bag by physically affecting the polymerizing fluid which can be accomplished in different manners dependent on what polymerizable fluid system that has been selected in accordance with the earlier discussions. According to one embodiment of the invention the polymerization is initiated by the influence of heat. The heating of the fluid can be generated by different means, such as irradiating the capsule with infrared radiation or by increasing the temperature of the rinsing liquid. According to a different embodiment, the polymerization process can be initiated substantially instantaneously by means of irradiation, preferably by means of exposing the eye to visible light, in particular to blue light.

The step of forming a lens implant can also involve a partial polymerization the polymerizable fluid, before final polymerization. In such case, refractive value can be controlled after a partial polymerization and compared with the predetermined value. If these values do not comply sufficiently, one or several of the mentioned adjustment steps can be performed until the refractive value of the eye agrees with the desired predetermined value. Indeed several partial polymerization processes are conceivable, each with a subsequent refraction control and optional adjustment. The partial polymerization preferably applies to a local polymerization of the fluid, even if selective partial polymerization into a homogenous semi-solid fluid is considered to be a part of this embodiment. The local polymerization can be accomplished by heating the capsular at a selected part, for example by directed infrared radiation. Alternatively, heated rinsing liquid can be directed to a region or site of the capsular bag for a time sufficient to complete a local polymerization process. For example, local polymerization can be employed to obtain a first sealing effect of the fluid filled capsular bag. For this purpose, a thin sealing shell-like solid part around the inner periphery of the capsular bag can be obtained by directing heated rinsing liquid for a suitable time around its outer periphery. A local polymerization around the opening or injection site can also be obtained, for example by polymerizing around the injection needle immediately after introducing the liquid into the capsular bag. By effectively sealing the capsular bag, it is possible to more safely conduct necessary adjustments without risking that the liquid leaks out of the injection site. Partial and local polymerization, as outlined above, can also be obtained by irradiation with suitable light, for example by focussing the light to the desired site. After conducting the step or steps of partial polymerization performing refraction control of the eye, the lens forming process is continued by a final polymerization. This final curing step will result in the permanent intraocular lens which now will provide the eye with refractive value complying with the predetermined value and a restored vision. It is preferred that the refractive value of the eye be kept constant, i.e. the shape of the capsular bag, during this final polymerization or during the entire formation step if no partial polymerization is conducted.

In certain embodiments, a method is provided of controlling the refractive value of the eye before, during, and/or after an ophthalmic surgery when the natural lens is replaced in the capsular bag by a polymerizable fluid. The control is exerted by the mentioned alternatives to modify the shape of the capsular bag into which a polymerizable fluid has been introduced.

As mentioned above herein, drugs may be administered in certain embodiments to control the state of accommodation of the eye in order to provide a predetermined accommodative state or condition in which a lens may be formed using a polymerizable fluid. Such drugs may also be used to maintain an accommodative state or condition in the eye for embodiments wherein an accommodative IOL is formed prior to implantation and then placed into the eye of a subject.

In certain embodiments, a method for controlling the amount of accommodation comprises administering to the mammal an effective amount of a muscarinic component, such as a muscarinic agonist or a muscarinic antagonist. Without wishing to limit the invention to any particular theory of operation, it is believed that the muscarinic component administered as described herein acts to at least assist or facilitate the ciliary muscle, for example, by effecting a parasympathetic response, or blocking or stimulating the parasympathetic system to obtain more effective ciliary muscle tone, in providing accommodation, for example, increased accommodation. This administering step preferably is effective to maintain the eye in an accommodative state.

A related application of the use of such muscarinic components is disclosed by Gwon et al. in U.S. Pat. No. 6,164,282, herein incorporated by reference. As disclosed by Gwon et al., an administering step may be effective to increase the tone of the ciliary muscle at a neutral resting state of the eye. As used herein, the term "neutral resting state" refers to the state of the eye which exists without visual stimuli, for example, in a totally darkened room or in a luminous but completely empty visual field. Such a "neutral resting state" can be considered the natural resting state of the eye. The neutral resting state of the eye can be referred to as "tonic accommodation," "space myopia," and "sky myopia." Viewed from a different perspective, the neutral resting state of the eye (with the natural crystalline lens present) exists with the eye focused for objects in a range of about one meter to about two meters from the eye.

In one useful embodiment, of the present invention a muscarinic component is administered and acts on one or more muscarinic (M) receptor subtypes of the ciliary muscle.

Muscarinic receptor subtypes enable selective contraction or relaxation of the circular or longitudinal fibers of the ciliary muscle by action on the $M_1$-$M_5$ receptor subtypes.

A summary of receptor subtypes is given in Table 1.

TABLE 1

| Receptor subtype | Tissue or cellular function | Signaling mechanism |
| --- | --- | --- |
| $M_1$ | Contraction or secretion | PI, Ca |
| $M_2$ | Relaxation | cAMP |
| $M_3$ | Contraction or secretion | PI, Ca |
| $M_4$ | Relaxation | cAMP |
| $M_5$ | Contraction or secretion | PI, Ca |

Where:
PI=Phosphoinositide hydrolysis (stimulatory response)
Ca=Increase in intracellular free calcium (Stimulatory response)
cAMP=Decrease in cyclic adenosine monophosphate (AMP) formation (inhibitory response)

The $M_3$ receptor subtype is the most common and is seen predominantly in the circular fibers and the $M_5$ receptor subtype is predominant in the longitudinal fibers. Accordingly, it is possible that the inhibition of the $M_5$ receptor subtype may allow the relaxation/stretching of the longitudinal fibers.

The compounds useful in practicing the present invention include any and all suitable muscarinic agonists or antagonists. As used herein, the term "muscarinic agonists" means any compound that stimulates a parasympathetic receptor subtype to generate a response. Parasympatholytic agents which block the parasympathetic system are muscarinic antagonists and parasympathomimetic agents which stimulate the parasympathetic system are muscarinic agonists. Neuro-effective junctions are considered cholinergic if energized by muscarinic agonists such as acetylcholine.

Without limiting the present invention to specific groups and compounds listed, the following is a list of representative muscarinic agonists and antagonists useful in the present invention:

Muscarinic Agonists

In general, muscarinic agonists are M nonselective and are parasympathomimetic and stimulate the parasympathetic system. Such muscarinic agonists include, but are not limited:
Pilocarpine
Isopilocarpine lactam
Carbachol
Bethanechol
Methacholine
Muscarine Muscarinic Antagonists Muscarinic antagonists are parasympatholytic and block the parasympathetic system.

These antagonists have higher affinity or selectivity for the designated receptor subtype, but they also bind to the other receptor subtypes with a lower affinity. Such muscarinic antagonists include, but are not limited to, in relation to M receptor subtypes:
M1: Pirenzepine, Telenzepine, trihexyphenidyl
M2: (+) (11-([2-[(diethylaminomethyl]-1-piperdidinyl} acetyl)-5,11-di-hydro-6H-pyrido(2,3-b)(1,4)benzodiazepine-6-one;
M3: diphenylacetoxy-N-methylpiperidine methiodide, (+) p-fluro-hexahydro-sila-difenidol hydrochloride
M4: Pirenzepine, Telenzepine.

Analogs of the foregoing compounds that function as muscarinic agonists are also specifically intended to be embraced by the present invention. The ability of such analogs to function in accordance with the present invention can be tested easily using no more than routine experimentation.

The methods in accordance with the present invention are particularly suited for subjects who are otherwise free of indications for ophthalmic treatments utilizing a muscarinic agonist or antagonist.

The muscarinic components in accordance with the present invention may be administered per se or in the form of pharmaceutically acceptable salts. When used in a formulation, the salts of muscarinic agonists and muscarinic antagonists should be both pharmacologically and pharmaceutically acceptable, but non-pharmaceutically acceptable salts may be conveniently used to prepare the active free compounds or pharmaceutically acceptable salts thereof.

Many of the compounds useful of the present invention are known in the art for other purposes, and are known to be safe under ordinary conditions of use. Thus, the treatment of this invention can be substantially conventionally administered, consistent with known eye treatments, and while avoiding irritation, discomfort or the need for unusual application procedures.

Compositions useful in the present invention may include any suitable formulation from which the presently useful muscarinic components may be delivered to the eye. Preferably, the muscarinic components useful in the present invention are topically administered or applied to the eye. By topical administration, the muscarinic components included in the formulations contact the surface of the eye and penetrate into the deeper tissues of the eye. Such formulations usually include liquid carriers and can be aqueous solutions or suspensions.

Preferably, the muscarinic components in accordance with the present invention are provided in formulations which enhance the duration of activity of the active material on neuro-effective junctions.

The muscarinic components in accordance with the present invention preferably are administered in pharmaceutically acceptable ophthalmic formulations. Such pharmaceutically acceptable ophthalmic formulation produces medically desirable therapeutic effects without concurrently causing clinically significant adverse effects. Clinically significant effects refer to unacceptable side effects of the formulation, including either medically or cosmetically unacceptable effects. Examples of unacceptable side effects include, but are not limited to, reddening or irritated eyes, impaired long distance vision, elevated intraocular pressure, or browache. With particular reference to pilocarpine, the doses utilized in the present invention fall below that which would cause such side effects.

The muscarinic components in accordance with the present invention are administered in therapeutically effective amounts. A therapeutically effective amount is one which at least assists or facilitates the ciliary muscle in providing accommodation, for example, positive and/or negative accommodation, preferably increased accommodation, in an eye including an artificial IOL. The muscarinic components are typically added to the formulations in accordance with the present invention in amounts in a range of about 0.001% and about 4% by weight of the entire formulation.

The muscarinic components in accordance with the present invention are preferably administered topically and delivered in a medically acceptable, substantially sterile, non-irritating ophthalmic formulation. Ophthalmic formulations may contain pharmaceutically acceptable concentrations of salts, buffering agents, preservatives, viscosity modifiers, osmotic agents and delivery enhancing agents.

Salts which can be used include, but are not limited to, sodium chloride, zinc sulfate, and potassium chloride. Buffers which can be used include, but are not limited to, boric acid and citric acid-based buffers. Preservatives which can be used include, but are not limited to, benzalkonium chloride and edetate disodium. Viscosity modifiers which can be used include, but are not limited to, methyl cellulose, glycerol, and polyethylene glycol. Osmotic agents which can be used include, but are not limited to, sodium chloride, mannitol and sorbitol. Delivery enhancing agents that facilitate the delivery of the therapeutic compound of the invention into the aqueous humor include, but are not limited to, substances which increase corneal permeability, such as surfactants, wetting agents, liposomes, DMSO, and the like. A wetting agent is a substance which facilitates corneal penetration by mildly disrupting the outer corneal surface. A preferred wetting agent is benzalkonium chloride. Other examples of wetting agents include sorbitan esters, polyoxyethylene ethers and the like. These additional materials preferably are present, if at all, in amounts effective to provide the desired benefit or property to the formulation.

It should be understood that although specific formulations have been defined, many variations are possible. The ophthalmic formulations useful in accordance with the present invention preferably are substantially nonirritating and non-damaging to the eye. Normally, such formulations can be applied in a liquid carrier, with an aqueous carrier being preferred although in some instances, quick dissolving forms of the medicaments may be administered in powder form or rubbed into the eye from applicators of various types. Spraying of the eye, the use of eye drops, and other methods of administration or application can be used.

Dosage levels vary greatly depending upon the individual to be treated and the specific medicament used. Proper dosing can be determined without undue experimentation and according to procedures well known to those of ordinary skill in the art.

The formulations preferably are packaged as sterile solutions in dropper bottles, as are well known in the trade. Other containers, including eye cups, can also be used.

The eye to which the muscarinic component is administered includes an artificial IOL, and in particular an artificial IOL adapted to be axially moved in the eye to provide accommodation. Such accommodating IOLs may include, but are not limited to, the IOLs disclosed in Levy U.S. Pat. No. 4,409,691 and Cumming U.S. Pat. Nos. 5,674,282 and 5,496,366. In a very useful embodiment, the accommodating IOL is adapted for bidirectional accommodating movement (both anteriorly and posteriorly in the eye) from an intermediate rest position in the eye. Such an IOL is disclosed in commonly assigned U.S. Pat. No. 6,176,878, which is herein incorporated by reference In a specific non-limiting example of this invention, a base solution can be formulated as follows (percentages by weight/volume (w/v)): sodium chloride 0.3%; edetate disodium 0.1%; boric acid 1.0%; benzalkonium chloride 0.01%; sodium hydroxide (adjust to pH 6.4) and water. Pilocarpine, at a concentration of 0.1% weight/volume, is added to the base solution.

The above formulation is administered to the eye of a 50-year old human adult which includes a monofocal IOL adapted to move axially in the eye to achieve accommodation. An increased range of axial movement in the eye, evidenced by an increased degree of accommodation, is apparent after administration of the eye drops.

When other muscarinic agonists and various muscarinic antagonists are substituted for pilocarpine, similar results are obtained.

An example of the formation of a lens using a polymerizable fluid will be given. In such embodiments, methods directed to refilling the natural human lens capsule with a polymerizable fluid are directed to securing that the intended post-operative refraction is achieved. One way is to adjust the lens power during the operation. Another way is to predict the amount of fluid and the refractive index of the fluid pre-operatively, which guarantee a correct post-op refraction. Within the context of the present invention it also is possible to combine both methods. In such a case, the appropriate volume and refractive index of the polymerizable fluid are determined prior to the surgical procedure, then during the operation, the refraction is further fine-tuned to the intended value. When the human lens is impaired, for instance by cataract or presbyopia, the impaired lens can be removed out of the lens capsule. Thereafter a polymerizable fluid can be injected into the capsule and polymerized. The new lens is molded by the capsule. The newly molded lens must have the correct lens power in order to give the patient the intended postoperative refraction. The lens power depends largely on the amount of injected fluid and the refractive index of the fluid. This means that the lens power can be controlled by these two parameters. Based on the predictions of the volume and refractive index for a specific patient, the surgeon can be provided a kit of materials at the operating table, from which he selects the right one for the specific patient. In the following example, a method is described which predicts the volume and refractive index of the polymerizable fluid, based on measurements on the individual patients and combined with data for the average human eye.

The determination is based on the combination of two sets of data:
1. General data of the human eye, measured on a representative population
2. Measurements of the individual patient.

1. General Data

Lens Thickness

The lens thickness is very much depending on age. Within an age group, the spread in lens thickness is very small. Shum, Ko, Ng and Lin (1993) measured the lens thickness of a group of 76 subjects of virtually the same age (s.d. 1.2 month). On an average lens thickness of 3.49 mm he found a standard deviation of 0.02 mm, which is 0.5%. The age relation of the lens thickness is best described by Koretz, Kaufman, Neider and Goeckner (1989), who found a relation of $$LT = 3.220 + 0.021 * A \quad (1)$$

LT=lens thickness [mm]
A=age [y]

When using this relation, the actual input for the calculation is age, and not lens thickness.

Relation Between Anterior and Posterior Lens Radius

The actual lens radii of an individual patient may differ a lot, however there is always a certain relation between the two. Based on measurements on human cadaver eyes, Glasser & Campbell (1999) found the relation of:

$$Rp = -0.261 * Ra - 2.631 \quad (2)$$

Rp=posterior radius [mm]
Ra=anterior radius [mm]

Relation Between Lens Equatorial Diameter and Lens Focal Length

The lens equatorial diameter is hidden behind the iris. It can not be measured with the equipment that is normally available in the ophthalmic practice. Therefore a reasonable estimate can be made, using the relation that was found by Glasser & Campbell (1999), based on measurements on human cadaver eyes:

$$LD = 0.0502 * FL + 5.288 \quad (3)$$

LD=lens equatorial diameter
FL=lens focal length

Relation Between the Natural Lens Focal Length and the Refilled Lens Focal Length The lens capsule and the lens do not need to have the same shape. As a result it is possible that after refilling the lens, the shape of the lens has changed. This was seen in calculations of lens refilling. This phenomenon also follows from the results of Glasser & Campbell (1999): For most lenses the focal length changes after decapsulation of the lens. However, this effect disappears at the age of 60 years, which corresponds to the age of full presbyopia. From this it can be concluded that the focal length of the refilled lens will be equal to the focal length of the original lens, provided that the refill material has the refractive index of natural lens material.

2. Measurements on the Individual Patient

Keratometer

With the keratometer, the cornea) power is measured. This is currently a standard measurement in cataract surgery. Alternatively, the corneal curvature (radius) can be measured.

The relation between corneal curvature and corneal power is:

$$K = 337.5/Rc \quad (4)$$

K=Corneal power [D]
Rc=Curvature radius of the cornea

A-Scan

With an A-scan, the axial dimensions of the eye can be measured. Also this is currently standard practice in cataract surgery. In general, it results in a measure of the anterior chamber depth and the total axial length of the eye.

Refraction and Refraction History

The refraction is measured by the optometrist. When the patient is currently blind, the refraction can not be measured. In such a case there are two alternatives:

1. The refraction history of the patients eye, during the period that the patient was not blind.
2. The refraction and/or the refraction history of the patient's fellow eye.

Calculation Scheme

1. Determination of the lens thickness, from the age of the patient.
2. Determining the radii of the lens, based on the known optical surfaces and refraction of the eye.
3. Determining the focal length of the natural lens.
4. Determining the lens equatorial diameter, based on the lens focal length.
5. Determining the volume of the natural lens.
6. Based on the desired post-op refractive outcome, select the appropriate refractive index.

The volume to be used is equal to the volume of the natural lens. The refractive index of the material is adapted, so that the predetermined refractive outcome for the patient will be reached.

Patient Data

Age: 63 year

| Results of the ophthalmic exam: | |
|---|---|
| Keratometer reading: | 43.7 Diopter |
| A-scan: Axial length | 23.35 mm |
| Anterior chamber depth | 3.25 mm |
| Historic refraction: | +2.5 Diopter spherical equivalent (stable). |

Accordingly, the calculations according to the calculation scheme are:

1. According equation (1), the lens thickness is 4.543 mm.
2. According equation (4), the cornea has a radius of 7.723 mm.

The length of the vitreous is the axial length, minus the anterior chamber depth and minus the lens thickness. So far the optical system is:

| Surface | Name | Radius | Thickness | Refractive Index |
|---|---|---|---|---|
| 1 | Cornea | +7.723 | 3.25 | 1.3375 |
| 2 | Lens | Ra | 4.543 | 1.422 |
| 3 | Vitreous | Rp | 15.557 | 1.336 |
| 4 | Retina | — | — | — |

Since, according to equation (2), Rp is a function of Ra, there is only one variable in this system. This variable can be solved, using the condition that it has to result in the known or historic refraction. Here a paraxial ray tracing procedure is used, adapted from the spreadsheet that is used to calculate A-constants for IOL's. This results in the lens radii: (Refraction Rx=spectacle refraction. For modeling the eye, the spectacle is made of Crown glass (Agarwal's principles of Optics and Refraction), 2 mm thick, with it's anterior surface 14 mm in front of the cornea).

Ra=12.286 mm
Rp=−5.838

3. The focal length of the natural lens is determined by the dimensions and refractive index:

Ra=12.286 mm
Rp=−5.838 mm
Thickness=4.543
Refractive index=1.422
The lens power (P), according the thick lens equation is 21.40 diopter and the focal length is 1336/P=62.425 mm.

4. Equatorial diameter, according equation (3) is 8.422 mm.

5. The volume of the lens, based on an ellipsoid, with the known thickness and equatorial diameter is 186.7 $mm^3$.

The volume of an ellipsoid is:

$$V = 4/3 * \pi * a^2 * b$$

With:
a=diameter/2
b=thickness/2

6. The refractive index can now be chosen for a specific post-operative refractive outcome. An index of 1.422 will result in the pre-op (historic) refraction of 2.5 diopter. The result of different refractive indices can be calculated by paraxial ray tracing, and results in the following table (Rx=post-op refraction):

| Rx | η |
|---|---|
| −3 | 1.457 |
| −2 | 1.451 |
| −1 | 1.445 |
| 0 | 1.439 |
| 1 | 1.432 |
| 2 | 1.426 |
| 2.5 | 1.422 |
| 3 | 1.418 |
| 4 | 1.411 |
| 5 | 1.403 |
| 6 | 1.395 |

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate methodologies and/or constructions from those described above that are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of restoring the vision of an eye by removing an impaired lens and replacing the lens with a polymerizable fluid, comprising:
   determining a refractive outcome for an eye;
   measuring one or more dimensions of the eye selected from the group consisting of corneal curvature, axial length of the eye, and anterior chamber depth prior to injecting a lens material in order to estimate the total volume of a capsular bag of the eye;
   from the estimate of the total volume of the capsular bag, calculating a quantity and refractive index of a polymerizable fluid to be introduced into the capsular bag;
   removing an impaired lens from the capsular bag;
   selecting the polymerizable fluid with the calculated refractive index; and
   injecting the calculated quantity of polymerizable fluid into the capsular bag.

2. The method of claim 1, further comprising selecting the polymerizable fluid from a kit of polymerizable fluids having a range of refractive indices.

3. The method of claim 2, wherein the kit has a range fluids having refractive indices varying from about 1.41 to about 1.6.

4. The method of claim 3, wherein the kit comprises a range of fluids filled in multi-compartment containers separately stored from agents necessary to bring about the polymerization.

5. The method of claim 4, wherein fluid communication is established between one or more of the compartments just prior to administration of the fluid to the capsular bag.

6. The method of claim 1, further comprising changing the refractive outcome of the eye by modifying a shape of the capsular bag and/or the calculated quantity of polymerizable material.

* * * * *